United States Patent [19]

Shimoda

[11] Patent Number: 4,590,800

[45] Date of Patent: May 27, 1986

[54] SPECIFIC GRAVITY INDICATOR

[75] Inventor: Keitaro Shimoda, Kusatsu, Japan

[73] Assignee: Nissho Corporation, Osaka, Japan

[21] Appl. No.: 653,739

[22] Filed: Sep. 24, 1984

[30] Foreign Application Priority Data

Sep. 22, 1983 [JP] Japan .................. 58-175870

[51] Int. Cl.$^4$ .............................................. G01N 9/10
[52] U.S. Cl. ......................................... 73/449; 73/440
[58] Field of Search ............... 73/440, 444, 447, 449, 73/451

[56] References Cited

U.S. PATENT DOCUMENTS

| | | | |
|---|---|---|---|
| 1,335,253 | 3/1920 | Midgley | 73/449 |
| 1,424,730 | 8/1922 | Linebarger | 73/440 |
| 2,133,300 | 10/1938 | Linebarger | 73/440 |
| 3,175,553 | 3/1965 | Mattson | 73/440 |
| 3,835,711 | 9/1974 | Kelly | 73/444 |
| 4,338,817 | 7/1982 | Callahan | 73/449 |

*Primary Examiner*—Stewart J. Levy
*Assistant Examiner*—Robert R. Raevis
*Attorney, Agent, or Firm*—Armstrong, Nikaido, Marmelstein & Kubovcik

[57] ABSTRACT

A specific gravity indicator used for measuring the specific gravity of an aqueous liquid, which is a shaped article comprising a styrene homopolymer and a styrene-butadiene elastomer and having a specific gravity of 1.005 to 1.035. By the specific gravity indicator, the specific gravity of an aqueous liquid such as urine at a standard temperature can be measured with a high accuracy at an arbitrary temperature.

6 Claims, No Drawings

SPECIFIC GRAVITY INDICATOR

BACKGROUND OF THE INVENTION

The present invention relates to a specific gravity indicator used for measuring the specific gravity of an aqueous liquid. More particularly, it relates to a specific gravity indicator which is used to measure the specific gravity of an aqueous liquid, particularly urine, by observing the status of the indicator in the liquid, namely, whether the indicator floats on the surface of the liquid, sinks into the liquid or suspends stationarily in the liquid without sinking and floating.

There is an areometer as one of simple specific gravimeter used for measuring the specific gravity of liquid. The measurement of specific gravity using the areometer has a problem that the measurement must be performed at a specified temperature, for instance, 20° C., which results in need of thermostat and troublesome operation.

In the past, the areometer was used for measuring the specific gravity of urine but is not used at present for the reasons mentioned above.

The common method used at present for determining the specific gravity of urine is one wherein the refractive index of urine is measured. The method utilizes the principle that the refractive index of urine is proportional to the total concentration of the urea, sodium chloride and potassium chloride contained in urine. Those substances are main components of urine. However, the ratio of the amount of urea to the total amount of sodium chloride and potassium chloride in urine varies every sample. For instance, in the case of the urine collected from a man who has eaten a salty food, the proportion of sodium salt is increased. Therefore, the error resulting from a deviation of the above-mentioned ratio from that of the standard urine is inherent in the method for determining the specific gravity of urine by measuring its refractive index. Furthermore, the method is not necessarily an easy method due to the need of refractometer.

The urine analysis is conducted with patients suffering from various diseases such as nephropathy and diabetes and post-operative patients. In that case, usually, urine is collected in a urinary drainage bag. It is convenient if there is a means for directly measuring the specific gravity of a urine collected in the urinary drainage bag.

SUMMARY OF THE INVENTION

It is an object of the present invention to provide a specific gravity indicator by which the specific gravity of an aqueous liquid at a given standard temperature can be measured at an arbitrary temperature.

Another object of the present invention is to provide a specific gravity indicator suitably used for measuring the specific gravity of urine.

Still another object of the present invention is to provide a specific gravity indicator which is used with being placed in a urinary drainage bag and by which the specific gravity of urine at a given standard temperature can be determined immediately after the urine is collected in the urinary drainage bag.

These and other objects of the present invention will become apparent from the description hereinafter.

The present invention provides a specific gravity indicator which is a shaped article comprising a styrene homopolymer and a styrene-butadiene elastomer and having a specific gravity of 1.005 to 1.035.

DETAILED DESCRIPTION

Generally, the specific gravity of a substance at a temperature of t°C. is defined as follows:

$$\text{Specific gravity} = \frac{\text{Density of a substance(g./cm.}^3\text{) at t° C.}}{\text{Density of a standard substance(g./cm.}^3\text{) at } t_0° \text{ C.}}$$

wherein $t_0°$ C. is a standard temperature.

In the case of liquid, in many cases, water is used as a standard substance and $t_0°$C. is 20° C., and the specific gravity of a liquid is defined as follows:

$$\text{Specific gravity} = \frac{\text{Density of a liquid at 20° C.}}{\text{Density of water at 20° C.}}$$

The specific gravity defined above is called "specific gravity (20° C./20° C.)". The specific gravity of urine is usually expressed by specific gravity (20° C./20° C.) thus defined. Therefore, in the case of obtaining the specific gravity (20° C./20° C.) of a liquid such as urine, the measurement is carried out 20° C.

When some body made of, for instance, a polymer, and having a specific gravity (20° C./20° C.) of G is thrown into a liquid kept at 20° C. and suspends in the liquid without sinking and floating, this shows that the liquid has the same specific gravity (20° C./20° C.) of G as that of the body. When the body floats on the surface of the liquid, this shows that the liquid has a smaller specific gravity (20° C./20° C.) than that (G) of the body. When the body sinks in the liquid, this shows that the liquid has a greater specific gravity (20° C./20° C.) than that (G) of the body.

The present invention is intended to utilize such a principle.

However, when the body is thrown in a liquid kept at a temperature different from 20° C., it is impossible to accurately determine the specific gravity (20° C./20° C.) of the liquid by observing such a status of the body in the liquid as mentioned above. The reason therefor is that, generally, the thermal expansion coefficient of a liquid to be measured is different from that of the body. If the thermal expansion coefficient of the body is the same as that of a liquid to be measured over some temperature range including 20° C. therein, the specific gravity of the liquid determined in the above manner shows the specific gravity (20° C./20° C.) so long as the measurement is carried out within the above temperature range. However, for instance, in the case that the body is made of some polymer and a liquid to be measured is an aqueous liquid, the specific gravity of the aqueous liquid determined in the above manner at a temperature of more than 20° C., for instance, 30° C., tends to be lower than the true specific gravity (20° C./20° C.) of the aqueous liquid, since, in the case of usual polymers, their thermal expansion coefficients are greater than that of water as the temperature increases.

In the present invention, it has been found out that a shaped article made of a mixture of a styrene homopolymer and a styrene-butadine elastomer, particularly a mixture of a styrene homopolymer had a styrene-butadiene elastomer wherein the ratio of the former to the latter is from 45/55 to 85/15 by weight, has substantially the same thermal expansion coefficient as that of water, particuarly urine, over the temperature range of 10° to 30° C.

Therefore, by employing the specific gravity indicator of the present invention which is a shaped article made of the specific polymer blend, the specific gravity of an aqueous liquid composed predominantly of water, for instance, urine, at a given standard temperature can be measured at an arbitrary temperature within the temperature range of 10° to 30° C.

Furthermore, a specific gravity indicator having an arbitrary specific gravity within the range of 1,005 to 1,035 can be obtained by selecting the blend ratio of the styrene homopolymer to the styrene-butadiene elastomer from the range of 45/55 to 85/15 by weight.

Moreover, the styrene homopolymer and the styrene-butadiene elastomer have a good compatibility with each other. Therefore, a uniform shaped article can be obtained by molding a blend of both.

Any usual grades of styrene homopolymers are used as the styrene homopolymer. Usually, the styrene homopolymer has a specific gravity of 1,04 to 1,07. As the styrene-butadiene elastomer, there are also used any usual grades of styrene-butadiene elastomers. However, a styrene-butadiene elastomer composed of 30 to 28% by weight of styrene unit and 70 to 72% by weight of butadiene unit and having a specific gravity of 0.94 to 0.96 is preferably employed.

In the present invention, it is preferable that the blend ratio of the styrene homopolymer to the styrene-butadiene elastomer is from 45/55 to 85/15 by weight. When the blend ratio deviates from the above range, the thermal expansion coefficient of the resulting blend tends to be different from that of water, particularly urine, even within the temperature range of 10° to 30° C. Usually, a blend polymer having a blend ratio of 45/55 by weight has a specific gravity of about 1.005 (20° C./20° C.) and a blend polymer having a blend ratio of 85/15 by weight has a specific gravity of about 1.035 (20° C./20° C.). On the other hand, usually, urine has a specific gravity of 1.005 to 1.035 (20° C./20° C.). From the view-point, usually, a blend polymer wherein the blend ratio deviates from the above range is not necessary to determine the specific gravity of urine.

Other additives such as pigments and delustering agents can be incorporated into the above-described blend polymer. These additives should be added in an amount such that the above-mentioned specific property relating to the fact that the thermal expansion coefficient of the blend polymer is substantially the same as that of water, particularly urine, is not hindered.

The specific gravity indicator of the present invention is produced by molding the above blend polymer into a shaped article. Injection molding is preferably adopted. Usually, the specific gravity indicator of the present invention is produced so that it has a given specific gravity (20° C./20° C.), since the specific gravity of urine is expressed by specific gravity (20° C./20° C.). A specific gravity indicator having a given specific gravity within an accuracy of about ±0.001 can be obtained.

The specific gravity indicator of the present invention may have various shapes such as sphere, cylinder, ellipsoid and disk. However, usually, a sphere having a diameter of 4 to 8 mm. or a disk having a diameter of 5 to 20 mm. and a thickness of 2 to 4 mm. is preferably employed.

In order to determine the specific gravity of an aqueous liquid such as urine, generally, a plurality of different color specific gravity indicators having different specific gravities from each other within the range of 1,005 to 1,035 are used. Usually, three or more kinds of the specific gravity indicators are employed and the statuses of the respective specific gravity indicators in the aqueous liquid are observed and the specific gravity of the aqueous liquid is determined from the results thereof. As the specific gravity indicators having smaller specific gravity difference between them are used, the specific gravity of the aqueous liquid is determined more accurately.

In such a manner, the specific gravity (20° C./20° C.) of an aqueous liquid, particularly urine, can be determined at an arbitrary temperature within the range of 10° to 30° C. with a high accuracy. The accuracy of the measurement is usually within ±0.002, preferably ±0.001, over the measuring temperature of 10° to 30° C., which satisfies the accuracy of the measurement required in the determination of the specific gravity of urine in clinical inspection. Usually, the error due to deviation of the measuring temperature from the standard temperature is within the range of ±0.001 and the error of the specific gravity of the specific gravity indicator per se is within the range of ±0.001.

The specific gravity indicator of the present invention is favorably applied to measuring the specific gravity of various aqueous liquids, for instance, aqueous solutions of inorganic or organic substances. The specific gravity indicator of the present invention is preferably applied to measuring the specific gravity of urine, which contributes to urine inspection in clinical test.

The present invention is more particularly described and explained by means of the following Examples. These Examples are intended to illustrate the invention and not be construed to limit the scope of the invention. It is to be understood that various changes and modifications may be made in the invention without departing from the spirit and scope thereof.

EXAMPLE 1

50 parts by weight of a styrene homopolymer having a specific gravity (20° C./20° C.) of 1.050 and 50 parts by weight of a styrene-butadiene elastomer (30:70 by weight) having a specific gravity (20° C./20° C.) of 0.950 were blended under heating and subjected to injection molding to give a sphere having a diameter of 6 mm. and a specific gravity (20° C./20° C.) of 1.005.

The sphere was thrown in three kinds of solutions of sodium chloride in water having different specific gravities (20° C./20° C.) shown in Table 1 and the status of the sphere in the solutions was observed at the temperatures shown in Table 1. The results thereof are shown in Table 1.

TABLE 1

| Specific gravity of NaCl solution (20° C./20° C.) | Measuring temperature (°C.) | Staus of the sphere |
| --- | --- | --- |
| 1.006 | 10 | Floated |
| 1.005 | 10 | Gradually sunk at a speed of 5 mm./min. |
| 1.005 | 20 | Balanced (Note) |
| 1.005 | 30 | Gradually floated at a speed of 6 mm./min. |
| 1.004 | 30 | Sunk |

Note: This means that the sphere suspended stationarily in the solution without sinking and floating (hereinafter the same).

As shown in Table 1, the sphere having a specific gravity (20° C./20° C.) of 1.005 naturally balanced in the solution having a specific gravity of 1.005 (20° C./20° C.) at a measuring temperature of 20° C. Further, the results of Table 1 reveal that the sphere would balance in a solution having a specific gravity (20° C./20° C.) between 1.005 and 1.006 at a measuring temperature of 10° C. and that the sphere would balance in a solution having a specific gravity (20° C./20° C.) between 1.005 and 1.004 at a measuring temperature of 30° C.

From the above facts, it is understood that the specific gravity (20° C./20° C.) of an aqueous solution of sodium chloride can be determined with an accuracy of ±0.001 over the measuring temperature range of 10° to 30° C. independently of the measuring temperature, by observing the status of the sphere in the solution.

EXAMPLE 2

The same procedures as in Example 1 except that the ratio of the styrene homopolymer to the styrene-butadiene elastomer was changed to 67/33 by weight were repeated to give a sphere having a specific gravity (20° C./20° C.) of 1.020. Employing the sphere, the same test as in Example 1 was conducted. The results are shown in Table 2.

TABLE 2

| Specific gravity of NaCl solution (20° C./20° C.) | Measuring temperature (°C.) | Status of the sphere |
|---|---|---|
| 1.020 | 10 | Almost balanced |
| 1.020 | 20 | Balanced |
| 1.020 | 30 | Almost balanced |

The results of Table 2 reveal that the specific gravity (20° C./20° C.) of an aqueous solution of sodium chloride can be determined with no error over the measuring temperature range of 10° to 30° C.

EXAMPLE 3

The same procedures as in Example 1 except that the ratio of the styrene homopolymer to the styrene-butadiene elastomer was changed to 83/17 by weight were repeated to give a sphere having a specific gravity (20° C./20° C.) of 1.035. Employing the sphere, the same test as in Example 1 was conducted. The results are shown in Table 3.

TABLE 3

| Specific gravity of NaCl solution (20° C./20° C.) | Measuring temperature (°C.) | Status of the sphere |
|---|---|---|
| 1.034 | 10 | Sunk |
| 1.035 | 10 | Gradually floated at a speed of 4 mm./min. |
| 1.035 | 20 | Balanced |
| 1.035 | 30 | Gradually sunk at a speed of 3 mm./min. |
| 1.036 | 30 | Floated |

The results of Table 3 reveal that the specific gravity (20° C./20° C.) of an aqueous solution of sodium chloride can be determined with an accuracy of ±0.001 over the measuring temperature range of 10° to 30° C.

Comparative Example 89 parts by weight of a low density polyethylene having a specific gravity (20° C./20° C.) of 0.926 and 11 parts by weight of titanium oxide (rutile type) were blended under heating and subjected to injection molding to give a sphere having a diameter of 6 mm. and a specific gravity (20° C./20° C.) of 1.015. Employing the sphere, the same test is an Example 1 was conducted. The results are shown in Table 4.

TABLE 4

| Specific gravity of NaCl solution (20° C./20° C.) | Measuring temperature (°C.) | Status of the sphere |
|---|---|---|
| 1.018 | 10 | Floated |
| 1.017 | 10 | Sunk |
| 1.015 | 10 | Sunk |
| 1.015 | 20 | Balanced |
| 1.015 | 30 | Floated |
| 1.013 | 30 | Floated |
| 1.012 | 30 | Sunk |

As shown in Table 4, while the polyethyene sphere having a specific gravity (20° C./20° C.) of 1.015 balanced in the aqueous solution of sodium chloride having a specific gravity (20° C./20° C.) of 1.015 at a measuring temperature of 20° C., it sunk or floated completely in the same solution at measuring temperatures of 10° C. and 30° C., respectively. Further, the results of Table 4 show that the sphere would balanced in an aqueous solution having a specific gravity (20° C./20° C.) between 1.017 and 1.018 at a measuring temperature of 10° C. and that the sphere would balanced in an aqueous solution having a specific gravity (20° C./20° C.) between 1.013 and 1.012 at a measuring temperature of 30° C.

From the above facts, it is understood that, in the case of determining the specific gravity (20° C./20° C.) of an aqueous solution of sodium chloride by employing the polyethylene sphere, the error at a measuring temperature of 10° C. or 30° C. is more than ±0.002, which is contrary to the purpose of the invention that it makes possible to determine the specific gravity of an aqueous solution with a high accuracy independently of measuring temperature.

EXAMPLE 4

Three kinds of the resin compositions shown in Table 5 were blended under heating and subjected to injection molding, respectively, giving a yellow disk having a specific gravity (20° C./20° C.) of 1.010, a blue disk having a specific gravity (20° C./20° C.) of 1.015 and a red disk having a specific gravity (20° C./20° C.) of 1.025. Each disk had a diameter of 14 mm. and a thickness of 3 mm.

TABLE 5

| | Yellow disk | Blue disk | Red disk |
|---|---|---|---|
| Components (parts by weight) | | | |
| Styrene homopolymer (Note 1) | 61.5 | 66.3 | 75.9 |
| Styrene-butadiene elastomer (Note 2) | 38.5 | 33.7 | 24.1 |
| Yellow pigment | Slight amount | — | — |
| Blue pigment | — | Slight amount | — |
| Red pigment | — | — | Slight amount |
| Titanium oxide (rutile type) | Slight amount | Slight amount | Slight amount |
| Specific gravity | 1.010 | 1.015 | 1.025 |

TABLE 5-continued

|  | Yellow disk | Blue disk | Red disk |
|---|---|---|---|
| (20° C./20° C.) | | | |

Note 1: Specific gravity (20° C./20° C.): 1.050
Note 2: Ratio of styrene content to butadiene content: 30/70 by weight, Specific gravity (20° C./20° C.): 0.950

A mixture of urea, sodium chloride and potassium chloride (1.000/0.575/0.200 by weight) was dissolved into water to prepare artificial urines having different specific gravities.

The statuses of the three kinds of the disks in the artificial urines were observed. The results are shown in Table 6.

TABLE 6

| Specific gravity indicator | Specific gravity of artificial urine (20° C./20° C.) | Measuring temperature (°C.) | Status of specific gravity indicator |
|---|---|---|---|
| Yellow disk | 1.011 | 15 | Floated |
| | 1.010 | 15 | Sunk |
| | 1.010 | 20 | Balanced |
| | 1.010 | 30 | Floated |
| | 1.009 | 30 | Sunk |
| Blue disk | 1.016 | 15 | Floated |
| | 1.015 | 15 | Gradually sunk |
| | 1.015 | 20 | Balanced |
| | 1.015 | 30 | Gradually floated |
| | 1.014 | 30 | Sunk |
| Red disk | 1.025 | 15 | Almost balanced |
| | 1.025 | 20 | Balanced |
| | 1.025 | 30 | Almost balanced |

From the results of Table 6, it is understood that in the case of each of the three kinds of specific gravity indicators, the specific gravity (20° C./20° C.) of artificial urine can be determined with an accuracy of better than ±0.001 independently of measuring temperature within the temperature range of 15° to 30° C.

EXAMPLE 5

The same three kinds of the specific gravity indicators as used in Example 4 were placed in a urinary drainage bag made from a laminate film of a polyester film and a polyethylene film.

An artificial urine having a specific gravity (20° C./20° C.) of 1.013 which was prepared in the same manner as in Example 4 was introduced into the urinary drainage bag. The statuses of the three kinds of specific gravity indicators were observed in the temperature range of 15° to 30° C. As a result, within the temperature range of 15° to 30° C., the yellow disk floated on the surface of the artificial urine, the blue and red disks sunk to the bottom of the bag.

Employing an artificial urine having a specific gravity (20° C./20° C.) of 1.014 which was prepared in the same manner as in Example 4, the same test as in the above was conducted. The statuses of the respective color disks in the artificial urine were the same as those in the above.

EXAMPLE 6

The same three kinds of the specific gravity indicators as used in Example 4 were placed in the same urinary drainage bag as used in Example 5.

A urine collected from a post-operative patient was introduced into the bag. The yellow disk floated on the surface of the urine, and the blue and red disks sunk to the bottom of the bag. From the results, it was determined that the specific gravity (20° C./20° C.) of the urine was between 1.010 and 1.015.

The specific gravity of the urine can be determined more accurately, for instance, by employing specific gravity indicators having smaller specific gravity difference of 0.002, and further 0.001, between them.

What is claimed is:

1. A specific gravity indicator used for measuring the specific gravity of an aqueous liquid, such as urine, which is a shaped article comprising a homogeneous mixture of a styrene homopolymer and a styrene-butadiene elastomer, having a specific gravity of 1.005 to 1.035, the ratio of the styrene homopolymer to the styrene-butadiene elastomer being from 45/55 to 85/15 by weight, the coefficient of thermal expansion of the shaped article being substantially the same as that of the aqueous liquid to be tested within the temperature range of 10° to 30° C.

2. The specific gravity indicator of claim 1, wherein the shaped article has a specific gravity of 1.005 to 1.035 when tested at 20° C. with water at 20° C. used as a standard.

3. The specific gravity indicator of claim 1, wherein the styrene-butadiene elastomer comprises 30 to 28% by weight of styrene and 70 to 72% by weight of butadiene, and the ratio of the styrene homopolymer to the styrene-butadiene elastomer is from 45/55 to 85/15 by weight.

4. The specific gravity indicator of claim 1, wherein the aqueous liquid to be tested is urine.

5. A specific gravity indicator used for measuring the specific gravity of an aqueous liquid, such as urine, comprising a plurality of different colored shaped articles having a homogeneous mixture of a styrene homopolymer and a styrene-butadiene elastomer, said plurality of different colored shaped articles having different specific gravities within the range of 1.005 to 1.035, the ratio of the styrene homopolymer to the styrene-butadiene elastomer being from 45/55 to 85/15 by weight, the coefficient of thermal expansion of the shaped articles being substantially the same as that of the aqueous liquid to be tested within the temperature range of 10° to 30° C.

6. A method of testing the specific gravity of urine consisting of:
A. obtaining a sample of the urine to be tested;
B. adjusting the temperature of the urine sample so it is within the range of 10° to 30° C.;
C. placing into the urine sample a plurality of different colored shaped articles comprising a homogeneous mixture of a styrene homopolymer and a styrene-butadiene elastomer, said plurality of different colored shaped articles having different specific gravities within the range of 1.005 to 1.035, the ratio of the styrene homopolymer to the styrene-butadiene elastomer being from 45/55 to 85/15 by weight, the coefficient of thermal expansion of the shaped articles being substantially the same as that of the urine sample to be tested within the temperature range of 10° to 30° C.; and
D. observing which of the colored shaped articles sink, float and are suspended in the urine sample, to determine the specific gravity of the urine.

* * * * *